United States Patent [19]

Walch

[11] Patent Number: 6,015,578

[45] Date of Patent: Jan. 18, 2000

[54] TRAPIDIL FOR USE IN THE THERAPY OF SYNDROME THAT MAY BE INFLUENCED BY IMMUNOMODULATORS

[75] Inventor: Hatto Walch, Laupheim, Germany

[73] Assignee: Rodleben Pharma GmbH, Rodleben, Germany

[21] Appl. No.: 08/945,216

[22] PCT Filed: Mar. 11, 1996

[86] PCT No.: PCT/EP96/01037

§ 371 Date: Oct. 9, 1997

§ 102(e) Date: Oct. 9, 1997

[87] PCT Pub. No.: WO96/32111

PCT Pub. Date: Oct. 17, 1996

[30] Foreign Application Priority Data

Apr. 13, 1995 [DE] Germany .......................... 195 14 048

[51] Int. Cl.[7] .................................................. A61K 9/20
[52] U.S. Cl. ........................................... 424/464; 424/465
[58] Field of Search ................................ 424/464, 181.1, 424/465

[56] References Cited

PUBLICATIONS

Bethke et al., "Effects of the Triazolopyrimidine Trapidil on Force of Contraction, Beating Frequency and Phosphodiesterase I–IV Activity in Guinea–pig Hearts[1)]", Arzneim.–Forsch./Drug Res., 1991, pp. 461–468.

Espevik et al., "A highly sensitive cell line, WEHI 164 clone 13, for measuring cytotoxic factor/tumor necrosis factor from human monocytes", Journal of Immunological Methods, 95 (1986), pp. 99–105.

Hansen et al., "Re–examination and further development of a precise and rapid dye method for measuring cell growth/cell kill", Journal of Immunological Methods, 119 (1989) pp. 203–210.

Lee et al., "Low–Molecular–Weight TNF Biosynthesis Inhibitors: Strategies and Prospectives", Wiley–Liss, vol. 44, No. 3, Nov. 1994, pp. 97–103.

*Primary Examiner*—Thurman K. Page
*Assistant Examiner*—William Edward Benston, Jr.
*Attorney, Agent, or Firm*—Ratner & Prestia

[57] ABSTRACT

Trapidil is used in the therapy of syndromes that may be influenced by immunomodulators. Trapidil is used for the preparation of a drug for the therapy or prophylaxis of diseases associated with TNF-induced pathological disorders.

19 Claims, No Drawings

TRAPIDIL FOR USE IN THE THERAPY OF SYNDROME THAT MAY BE INFLUENCED BY IMMUNOMODULATORS

This application is the U.S. national-phase application of PCT International application Ser. No. PCT/EP96/01037.

The present invention relates to the use of Trapidil (Trapymin) for preparing drugs suitable for the therapy of diseases which may be influenced favourably by the action of an immunomodulatory active ingredient. Chemically, the substance Trapidil is an N,N-diethyl-5-methyl-s-triazolo[1,5-a]-pyrimidine. Its clinical-pharmacological activity as known so far extends to the treatment of coronary cardiac diseases both in case of acute attacks as well as prophylaxis and long-term administration in case of this chronic disease. Trapidil, which acts as an anti-ischaemic agent, is not comparable with other coronary dilators and the remaining anti-angina coronary therapeutic agents of the prior art, for example the nitrates or nitro compounds such as nitroglycerine or isosorbide dinitrate, the β-receptor blockers such as propranolol or calcium antagonists (Nifedipin), either with regard to its clinical spectrum of activity or its chemical structure.

In view of its triazolo[1,5-a)-pyrimidine structure, Trapidil holds a special position among coronary therapeutic agents, because it is the only active ingredient with this particular ring structure in this series of drugs. From the group of triazolo pyrimidines, only 1,4-dihydro-5-(2-propoxyphenyl)-7H-1,2,3-triazolo[4,5-d]-pyrimidine-7-one has been tested experimentally as an anti-asthmatic agent; the less common 5-amino-1,6-dihydro-7H-1,2,3-triazolo[4,5-d]-pyrimidine-7-one, also known as 8-azaguanine, is known as a cytostatic drug.

Experiments on the myocardium of animals (T. Betke, H. Mehl, W. Meier, W. Schmitz et al.: "Effects of the Triazolopyrimidine Trapidil on force of contraction, beating frequency and phosphodiesterase I–IV activity of guinea pig hearts", Arzneimittelforschung 41/5, p. 461–468, 1991) have shown that Trapidil inhibits the phospodiesterases I–IV, i.e. is an unspecified inhibitor of the isoenzymes PDE I–IV. This is in contrast to the specific PDE-inhibitors in the form of methyl xanthines, for example pentoxifylline, which is a specific inhibitor of the PDE III isoenzyme. This activity stands for an antagonistic effect with a view to the adenosine receptor. In other words, adenosine receptors are not influenced by Trapidil, which was shown by the experiments conducted by E. G. Krause "Hemmung der Isoenzyme der Phosphodiesterase aus Herzmuskel, glatter Muskulatur und Thrombozyten durch Trapidil" (Inhibition of isoenzymes of phosphodiesterase from the myocardium, non-striated muscles and thrombocytes by Trapidil) (cf. Trapidil Workshop, June 28/29, 1991 in Munich).

From Circulatory Shock, 44, pages 97–103 (1995), it is also known that pentoxifyllin may have advantages in case of bacterial infections or malaria of the mouse in connection with a TNF-α-inhibiting activity. It is also generally known that pentoxifyllin, a xanthine derivative having a completely different chemical structure from Trapidil, primarily activates circulation in the peripheral vessels. Thus, the circulatory activity of Trapidil with its effect on the coronaries is completely different from the action profile of pentoxifyllin.

In view of this specific action of Trapidil on the activity of the coronaries, it was surprising to find now that this triazolopyrimidine derivative has a favourable effect on a series of syndromes which respond to a substance with immunomodulatory activities. This includes a number of syndromes that occur in connection with infections, neoplasms and patho-immunogenic diseases. In particular, we have found unexpectedly that Trapidil has a tumour necrosis factor (TNF-α)-inhibiting activity.

In general, the TNF is a cytokine such as IFN-γ, IL and CSF which are formed by different types of cells such as monocytes or macrophages. This factor has a wide spectrum of biological activities which play a role in the response of the organism, for example, to infections, neoplasms and pathoimmunogenic diseases. These include, for example, an increased proagulating activity at the endothelium, extravasation, cytokine (IL-1, IL-8, CSF) synthesis as well as PAF synthesis and an increased number of adhesion molecules. On leukocytes, the TNF causes an increase of neutrophilic degranulation, oxygen radicals, cytokine (IL-1, CSF) synthesis and influences the prostacyclin $E_2$ formation. The TNF activity is also evident in the lung, where an increased capillary permeability, formation of oedemas as well as adhesion and activation of leukocytes are recorded.

TNF also attacks both the liver where the formation of so-called acute phase proteins is increased and the muscles, where the protein degradation is increased and the glycogen content reduced. In addition, TNF causes feverish symptoms on the central nervous system which are accompanied by increased anorexia and ACTH release. From these activities, we can draw the conclusion that the TNF plays a substantial role with regard to the resistance of the organism against foreign organisms and tumour cells.

Thanks to the TNF-inhibiting activity of Trapidil, a series of novel indications result for this active ingredient, which per se acts on the coronaries.

Thus, especially those syndromes may be influenced favourably by the administration of Trapidil which develop in connection with the TNF mediator effect in inflammatory processes, for example processes mediated by leukocyte-derived cytokines of the interleukin (IL) type.

Therefore, the administration of Trapidil is indicated in case of lung failure, multiple organ failure as a result of septic shock (ARDS/acquired respiratory distress syndrome), cachectic lung disease, pneumonitis, peritonitis, cachectic conditions in connection with the HIV syndrome and the acute phase of virus re-duplication, as well as cachectic conditions in connection with tumours, diseases of the central nervous system, for example in case of cerebral malaria (clinical outcome) or multiple sclerosis to reduce the activity of the disease or exert a favourable influence on MS episodes, in case of vascular headache (suppression of local TNF production), contact eczemas, psoriasis or neurodermitis in connection with the inhibition of local TNF genesis. Further possible indications are sclerodermia, diabetic triopathy (neuropathy, retinopathy and nephropathy), as well as keloids and morphoea. Additional diseases which may be influenced favourably by the administration of Trapidil are lymphatic oedemas, myx oedemas, sclerodermia, calcinosis cutis, Kawasaki disease, disorders caused by the deposition of immunocomplexes such as rheumatoid arthritis, systemic lupus erythematodes, periarteritis nodosa, poly- and dermatomyositis, diffuse fibrotic alveolitis, certain forms of glomerulopathy, lepra, trypanosomiasis, chronic-aggressive hepatitis and Dengue fever, as well as the Joop Buckley syndrome which is an immunodeficiency syndrome in connection with IgE hyperimmunoglobulin, and xanthomatoses or sarcoidosis.

The above-mentioned immunomodulatory activity is also connected with the interleukin-inhibiting activity which we found unexpectedly. Unless already taken into account among the above novel medical indications of Trapidil, this active ingredient has also shown a positive influence in the following syndromes: loss of appetite, damages as a result of dialysis such as dialysis arthropathy, dialysis osteopathy or other dialysis incompatibilities or damages, endotoxic shock, toxic shock syndrome, cachexia, myalgia caused by infections, osteoporosis, rheumatic arthritis, gouty arthritis as well as morbus Crohn and colitis ulcerosa.

Transplantation-related GVH reactions may also be influenced positively by Trapidil in connection with bone marrow transplantations. This also applies in case of kidney transplantations with regard to relieving OTK-3 side effects by administering this active ingredient.

However, lesions caused by physical traumas—be they of mechanical origin like lacerations, contusions or wounds, be they injuries caused by thermal action on the body tissue, for example burns or frostbite, or traumas caused by electricity—may also be treated with Trapidil. The same applies for the detrimental effects of irradiation, be they X-rays, ultraviolet rays, infrared rays or $\gamma$-rays.

By treatment with drugs containing Trapidil, all kinds of infectious diseases caused by bacteria, bacilli, fungi, viruses or parasites may also be influenced positively. In addition, symptoms caused by the detrimental effect of environmental toxins such as heavy metal, asbestos, beryllium, chromium or mercury compounds as well as intoxication caused by herbicides or pesticides may be alleviated.

Due to the above-mentioned TNF-$\alpha$-inhibiting activity, Trapidil is particularly well suited for a therapy with medicaments which cause release of the tumour necrosis factor (TNF). This permits suppression of the side effects of such TNF-releasing substances, for example from the series of macrolide and polyene antibiotics which have some antimycotic activity, especially those obtained from streptomyces species such as streptomyces nodosus, streptomyces noursei or streptomyces antibioticus. In case of treatment with cyclosporine A, it is possible to reduce the nephrotoxicity by the additional administration of Trapidil.

Thus, this combination therapy permits treatment which is harmless under toxicological aspects. Trapidil itself may also be used directly with the tumour necrosis factor TNF, for example in the therapy of neoplasms, avoiding acute damage to the lung and hypotension. Trapidil administration may also be considered in case of acute kidney failure after reperfusion of the kidney.

It has also been found that Trapidil has a beneficial effect in the treatment of proliferating skin diseases, for example atopic, unspecified or allergic contact dermatitis, basal or scaly skin carcinomas, ichthyosis diseases, hyperkeratoses, pre-malignant sun-keratosis or other keratoses, acne as well as seborrhoic dermatitis.

Quite unexpectedly, neurological disorders such as morbus Parkinson or epilepsy may also be favourably influenced by the administration of Trapidil.

The individual Trapidil dosages used for therapy or prevention are between 10 mg and 500 mg; the total daily dosage is between 50 mg and 3.000 mg in case of oral administration, between 1 mg and 10 mg per kilogram bodyweight in case of intravenous administration and between 250 and 3.000 mg per individual topical application. The preferred dosages are 100 mg to 600 mg per day in case of oral or parenteral administration; 50 mg, 100 mg, 200 mg, 300 mg, 400 mg or 500 mg are especially preferred single dosages.

The same dosages in form of individual or daily doses are also recommended when combining Trapidil with other active ingredients. One of the combination variations of Trapidil is the joint or separate administration in connection with corticosteroids which are used in individual doses between 0.01 mg to 300 mg depending on the type of glucocorticoid used such as prednisolone, prednisone, hydrocortisone (cortisone), dexamethasone, cortisone, triamincolone, betamethasone, individual doses of 0.5 mg, 1 mg, 2 mg, 5 mg, 10 mg, 50 mg, 100 mg, 200 mg or 500 mg are possible. The daily dosages may go as high as the double, triple or quadruple amount and may be between 1 mg and 1000 mg.

Other advantageous combinations also result from the joint or separate administration of Trapidil together with interferons, for example, $\alpha$, $\beta$ or $\gamma$-interferon of type I which is administered in an amount of 0.1 to $100 \times 10^6$ IU. A preferred individual interferon dose are 1, 3, 5, 10 or $20 \times 10^6$ IU per application or the double, triple or quadruple amount as daily dosage. If Trapidil is to be used to suppress TNF-induced side effects, the above individual or daily dosages are recommended, the drug causing TNF-induced damages being administered in the customary amount of, for example, 0.1 mg to 1 mg/kg bodyweight per day or as single dose of 50 mg of lyophilisate for infusion in case of a macrolide or polyene antibiotic or antimycotic agent.

In the therapy of neoplasms, Trapidil is also used in the above-mentioned daily or individual doses. In case of direct administration of the tumour necrosis factor TNF itself, the single or daily dosage of the latter active ingredient is between 0.5 and $10 \times 10^6$ IU per kilogram bodyweight.

The preparation of drug forms, namely both of the single substance preparations having a Trapidil content and the combination preparation containing Trapidil together with other ingredients, especially one or several of the above-mentioned drugs, is carried out in the conventional manner. In case of combination preparations, the individual single doses may be combined directly depending on their compatibility with each other or be present in separate form in one drug package. This permits their application either by single administration side by side or, in case of the separate form, one after the other. This latter possibility is particularly suited for such drug forms where the joint administration of the different active ingredients would cause chemical or pharmacological incompatibilities or where different forms of administration must be selected on the basis of specific pharmacokinetic conditions. In such cases, one active ingredient may, for example, be administered orally and the other parenterally, optionally at different times.

For peroral administration, tablets, sugar-coated tablets, sustained-release tablets, capsules, film-coated tablets, powders, chewing gum or liquid forms such as suspensions, elixirs or solutions may be used. For mucous administration, sublingual forms such as tablets, chewing gum etc. are suitable. Another form of mucous administration is the application of suppositories. Parenteral administration may take place by the intravenous or interarterial route. For this purpose, aqueous injection or infusion solutions are suitable which are prepared by means of sterile filtration. For topical-systemic application of Trapidil, transdermal drug forms such as plasters may be used.

Sustained-release tablet

| Composition/Ingredients | mg/tablet |
|---|---|
| Trapidil | 300.00 |
| Sodium alginate | 150.00 |
| Lactose · 1H$_2$O | 110.00 |
| Poly-(1-vinyl-2-pyrrolidone) | 20.00 |

| Composition/Ingredients | mg/tablet |
|---|---|
| Purified water | 23.20 |
| Talcum | 10.80 |

The sodium alginate may be substituted by other hydrophilic skeleton substances such as cellulose derivatives (e.g. hydroxyethyl cellulose, hydroxypropyl cellulose, methylhydroxypropyl cellulose, polyacrylic acid and/or polyvinyl alcohol).

Depending on the requirements of the patient, the dose of the active ingredient may be varied within the framework described above. When making such variations, the amounts of excipient must be adjusted accordingly. In individual cases, however, the individual dose may be up to 700, 800, 900, 1000, 1100 or 1200 mg in the sustained-release form.

Suitable excipients for any solid or liquid drug forms are cellulose or cellulose derivatives, gelatine, starch or sugars such as lactose, sucrose, sorbitol, mannitol or water-insoluble inorganic substances such as dicalcium phosphate or calcium phosphate, glucose, rupturing agents, emulsifiers, dispersants or suspending agents as well as binders such as sodium carboxymethyl starch, carboxymethyl cellulose, calcium and other cellulose derivatives, alginic acid, polyvinyl pyrrolidones, gelatine, starch, alginates or polyethylene glycols (polywaxes) or lubricants and anti-adhesive agents. If necessary, stabilisers, colouring and aroma agents, preservatives or buffer substances are added to provide isotonicity and chemical stability. It is also possible to use various excipients in order to control a specific release rate in case of solid oral drug forms or a suitable grain size distribution of the active ingredients which result in a certain release picture.

For topical administration, ointments, creams of oil in water or water in oil and amphiphilic systems, microemulsions as well as gels and pastes and lotions are suitable. When preparing these drug forms intended for external administration, customary additives such as skin-compatible solvents like water, ethanol or isopropanol as well as polyhydric alcohols such as propylene glycol or glycerol are used. Suitable substances providing consistency or solubilisers are cellulose ether, long-chained fatty alcohols as well as ethoxylations products, long-chained fatty acids, hydrogenated peanut oil, semi-solid lipids such as wool wax, paraffin oil or solid or semi-solid paraffin, ester or oleic, palmitinic and/or myristic acid as well as semi-synthetic middle-chained triglycerides, polyglycols or vaseline. Among suitable emulsifiers or surfactants are compounds from the series of polyhydric alcohols partially esterified with long-chained fatty acids (of the glycerol monostearate type), polyoxyethylated derivatives of these compounds (of the Tagat® S2 type), sorbitan fatty acid esters (of the Span® or Arlacel® type) polyoxyethylated derivatives of these compounds (of the polysorbate type=Tween®), fatty acid esters of the polyoxyethylene type (Myrj® type) and fatty alcohol esters of polyoxyethylene (Brij® type).

The novel effectiveness of Trapidil shown above was found on the occasion of tests for determining the cytokine release and measuring the TNF activity. The quantitative determination of the cytokine release was carried out in a bioassay using WEHI 164 subclone 13 (fibrosarcoma lysating assay) as described by T. Espevik & J. Nissen-Meyer in: "A highly sensitive cell line, WEHI 164 clone 13, for measuring cytotoxic factor/tumour necrosis factor from human monocytes", J. Immunol. Methods. 95 (1986), page 99 et seq. In this test, samples of pure dilutions containing the hybridoma cells are incubated for 20 hours before conducting the MTT test, as can be taken from the publication by M. B. Hanssen, S. E. Nielsen and K. Berg: Re-examination and further development of a precise and rapid dye method for measuring cell growth/cell kill. J. Immunol. Methods, 119 (1989), page 203 et seq. The cultivated plates were then measured at 540 nm in a micro ELISA measuring device (MR 580, Dynatech Laboratories, Inc. Alexandria, Va., U.S.A.). The values thus obtained on the α-TNF formed were expressed in pg/mm using an internal standard of human recombinant TNF-α (Boehringer, Mannheim, Federal Republic of Germany).

In another test, resident peritoneal mouse macrophages in a quantity of $2\times10^5$ were pre-incubated in 0.2 ml of Iscove medium with the test substances for 20 minutes. Then the cytokine formation was induced through incubation with lipopolysaccharide in an amount of 100 ng/ml from salmonella abortus equi for a period of four hours. After that, the TNF was quantitatively determined in the cytotoxicity determination process on the basis of WEHI cells. After these preparations, inhibition by Trapidil in concentrations between 1 and 10,000 μmole could be conducted systematically. Surprisingly it was found that Trapidil has a dosage-dependent inhibiting effect on TNF synthesis. It was possible to transfer this in vitro finding to clinical and in vivo conditions.

What is claimed is:

1. A method for the therapy of diseases which respond to substances with immunomodulatory activity comprising administration to a patient a drug comprising Trapidil as an immunomodulating active ingredient.

2. A method for treating diseases which are related to TNF-related pathological disturbances comprising administration of Trapidil to retard TNF-α activity along with medicine used to treat the disease.

3. The method according to claim 2 wherein the disease is associated with leukocyte-derived cytokins of the tumour necrosis factor (TNF).

4. The method of claim 2 wherein the Trapidil dosage units in drug form are between 10 mg and 500 mg.

5. The method of claim 2 wherein a compound of the interferon is administered additionally by one of, in combination with the Trapidil or by separate administration.

6. The method of claim 2 wherein an active ingredient promoting TNF production is administered in addition to the Trapidil by one of jointly or separately side by side.

7. The method of claim 2 wherein, in addition to the Trapidil, a glucocorticoid is administered in combination therewith by one of jointly or separately.

8. The method for treating diseases according to claim 2 wherein the diseases are associated with leukocyte-derived cytokins of the tumour necrosis factor (TNF).

9. The method according to claim 8 wherein the Trapidil dosage units in drug form are between 10 mg and 500 mg.

10. The method according to claim 8 wherein a compound of the interferon is applied additionally by one of, in combination with the Trapidil jointly or by separate administration.

11. The method according to claim 8 wherein an active ingredient promoting TNF production is administered in addition to the Trapidil by one of jointly or separately side by side.

12. The method according to claim 8 wherein, in addition to the Trapidil, a glucocorticoid is administered in combination therewith by one of jointly or by separate administration.

13. The method according to claim 3 wherein the Trapidil dosage units in drug form are between 10 mg and 500 mg.

14. The method according to claim 3 wherein a compound of the interferon is administered additionally by one of, in combination with the Trapidil jointly or by separate administration.

15. The method according to claim 3 wherein an active ingredient promoting TNF production is administered in addition to the Trapidil by one of jointly or separately side by side.

16. The method according to claim 3 wherein, in addition to the Trapidil, a glucocorticoid is administered in combination therewith by one of jointly or by separate administration.

17. The method according to claim 4 wherein a compound of the interferon is administered additionally by one of, in combination with the Trapidil jointly or by separate administration.

18. The method according to claim 4 wherein an active ingredient promoting TNF production is administered in addition to the Trapidil by one of jointly or separately side by side.

19. The method according to claim 4 wherein, in addition to the Trapidil, a glucocorticoid is administered in combination therewith by one of jointly or by separate administration.

* * * * *